(12) United States Patent
Ross

(10) Patent No.: US 6,280,188 B1
(45) Date of Patent: Aug. 28, 2001

(54) DENTAL LIGHT FILTER

(76) Inventor: Gilbert J. Ross, P.O. Box 7134, Christiansted, St. Croix, VI (US) 00823

(*) Notice: Subject to any disclaimer, the term of this patent is extended or adjusted under 35 U.S.C. 154(b) by 0 days.

(21) Appl. No.: 09/542,860

(22) Filed: Apr. 4, 2000

(51) Int. Cl.[7] ............................................. A61C 3/00
(52) U.S. Cl. ............................................. 433/29; 433/229
(58) Field of Search ........................... 433/29, 141, 229; 359/892, 893, 889; 160/24

(56) References Cited

U.S. PATENT DOCUMENTS

| | | | |
|---|---|---|---|
| D. 298,965 | 12/1988 | Friedman | D24/10 |
| D. 345,618 | 3/1994 | Gonser et al. | D26/63 |
| 2,444,520 | 7/1948 | Marsh . | |
| 2,464,954 | 3/1949 | Werth . | |
| 2,563,473 | * 8/1951 | Levinson | 433/29 |
| 3,584,910 | * 6/1971 | Lupul | 296/97 |
| 4,398,585 | * 8/1983 | Marlow | 160/23.1 |
| 4,640,685 | 2/1987 | Croll | 433/141 |
| 4,655,712 | 4/1987 | Croll | 433/229 |
| 4,662,842 | 5/1987 | Croll | 433/141 |
| 4,744,403 | * 5/1988 | Hausman et al. | 160/272 |
| 4,775,918 | 10/1988 | Snyder | 362/18 |
| 4,813,198 | * 3/1989 | Johnston et al. | 52/171 |
| 5,443,923 | * 8/1995 | Laniado et al. | 428/476.1 |
| 5,509,800 | 4/1996 | Cunningham et al. | 433/29 |

FOREIGN PATENT DOCUMENTS

| | | |
|---|---|---|
| 605145 | 5/1926 | (FR) . |
| 14682 | of 1913 | (GB) . |
| 14683 | of 1913 | (GB) . |
| 324733 | 2/1930 | (GB) . |
| 433337 | 8/1935 | (GB) . |
| 482331 | 3/1938 | (GB) . |
| 500234 | 2/1939 | (GB) . |
| 1206260 | 9/1970 | (GB) . |
| 453100 | 11/1949 | (IT) . |

* cited by examiner

*Primary Examiner*—John J. Wilson
*Assistant Examiner*—Melba Bumgarner
(74) *Attorney, Agent, or Firm*—Oblon, Spivak, McClelland, Maier & Neustadt, P.C.

(57) ABSTRACT

A light-filtering apparatus is provided for attachment to a dental lamp. The apparatus includes a filter that blocks out light having a 350 to 550 nanometer wavelength. A spring-loaded roller is configured to carry the filter. A second roller may also be provided. A window-like frame is attached to a center of rotation of either the spring-loaded roller or the second roller. A tab is attached to the filter and is configured to place the filter in front of the dental lamp when the tab is pulled by a user. Essentially, the apparatus functions in a manner similar to a window shade for alternately blocking out and allowing light to shine on either a composite resin or another light-curable material that is being placed in a dental patient's mouth.

18 Claims, 2 Drawing Sheets

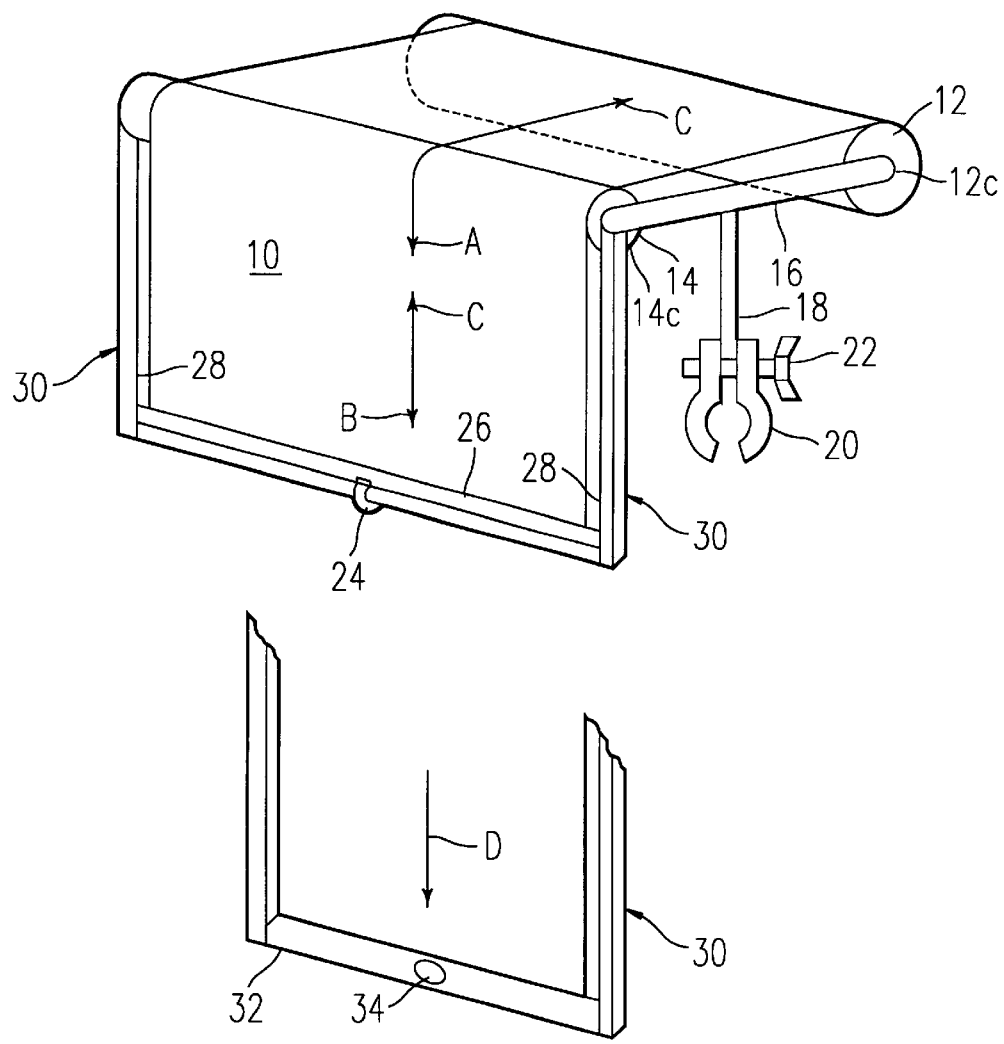
FIG. 1
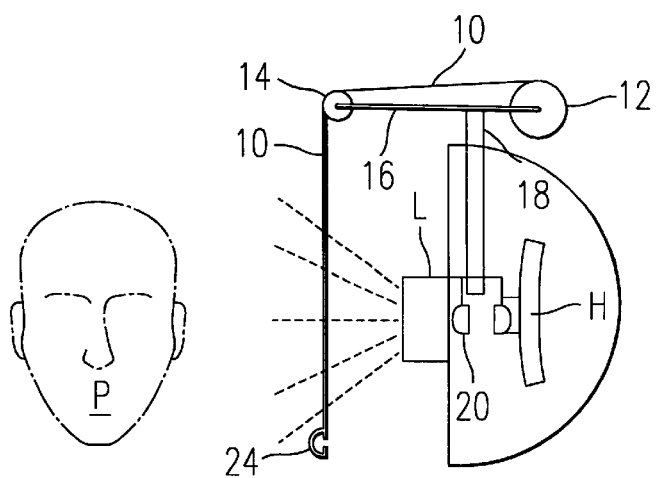
FIG. 2
FIG. 3

DENTAL LIGHT FILTER

BACKGROUND OF THE INVENTION

1. Field of the Invention

This invention relates to a light-filtering apparatus, in particular for a dental lamp.

2. Description of the Related Art

One of the problems that exists in the modern dental office occurs while working with light-cured composite resins under a standard operatory light. Light-cured composites have been one of the greatest advancements in modern dentistry because they allow the dentist easy placement of tooth-colored fillings in teeth. However, the one characteristic that makes such composites so versatile and workable, i.e. their ability to set up and be cured when illuminated by a 350 to 550 (usually 400 to 500) nanometer (nm) wavelength of light, also makes the composites vulnerable to premature hardening by the standard operatory light.

To cope with this problem, the dentist must either work very quickly or turn the operatory light away from the tooth where the composite is being placed. Neither choice is ideal for a quality dental procedure because working quickly may result in mistakes, such as leaving voids. Likewise, by turning the light away to stop the curing process, the dentist has a difficult time seeing what he or she is doing, especially in the placement of posterior composites.

One way to solve the problem is to develop composites which take longer to cure. A simpler way to solve the problem is to filter out the 350–550 nm wavelength that is emitted from the operatory light. By doing so, the dentist can work at a normal pace and still have almost 90% illumination on the subject tooth.

One such solution was proposed by Dr. Theodore P. Croll of Doylestown, Pa., in his U.S. Pat. No. 4,640,685 which issued to him on Feb. 3, 1987, for a hand-held light-filtering paddle. His invention is intended to protect the dentist's eyes from the light wavelength emitted by the light-curing gun. However, the disadvantage of this device is that the dentist is left with only one free hand to work.

Dr. Croll shortly thereafter obtained U.S. Pat. No. 4,662,842 which issued to him on May 5, 1987, for a finger-mounted light filter. Again, the filter is intended to protect the dentist's eyes from the curing light. However, while permitting the free use of both hands, the dentist is unable to reach into the patient's mouth with the filter secured on one finger.

Drs. Cunningham and Leggo of Australia later obtained U.S. Pat. No. 5,509,800 which was granted on Apr. 23, 1996, for a filter which is detachably fitted in front of a dental lamp by an attachment device. Because their filter attaches to the actual light housing itself, it is difficult, if not impossible, to attach the filter to most lights. However, the main drawback of this development is that the filter must be handled each time when it is used and it must be placed somewhere when it is not in use. Thus, a new problem of cross contamination between patients and staff members is created.

Thus, it remains a problem in the prior art to provide a dental filter which permits the dentist to have free use of both hands and which simultaneously prevents cross contamination between patients and staff members.

SUMMARY OF THE INVENTION

A primary object of the present invention is to provide a dental filter which permits the dentist to have free use of both hands and which simultaneously prevents cross contamination between patients and staff members.

The present invention is a filter that is attached to a handle of a dental lamp and has a support structure that frames the dental lamp. The filter material is cellophane-like and will both easily and simply roll up out of the way when not wanted, but will still be immediately ready to use when needed again. Essentially, the invention resembles a window shade.

The present invention allows virtually no handling of the filter, except for the touching of a disposable tab that is positioned on a cross bar of a filter roll.

Thus, the present invention eliminates the problem of cross contamination between patients and staff members simply and effectively because the entire filter mechanism does not need to be sterilized or disinfected between patients.

Because there is only a small amount of filter on each roll, the invention basically operates like a window shade. The one-piece unit is simply pulled down by the user and is then rolled back up after the dental work is finished. When the filter roll tears or breaks, a new one is mounted in its place and the old one is properly discarded as medical waste.

Furthermore, unlike the prior art devices of Croll and Cunningham et al., the filter device of the present invention does not need to be stored or placed somewhere when not in use because the filter is simply rolled up on a roller out of the way, but remains ready for use again at the fingertips of either the dentist or a dental assistant.

A more complete appreciation of the invention and its advantages will be readily obtained as the device becomes better understood by reference to the following detailed description when considered in connection with the accompanying drawings.

BRIEF DESCRIPTION OF THE DRAWINGS

FIG. 1 shows a perspective view of a first embodiment of the invention.

FIG. 2 shows a perspective view of a bottom frame of the first embodiment.

FIG. 3 shows a side elevational view of the first embodiment.

DETAILED DESCRIPTION OF THE INVENTION

Figure 4:
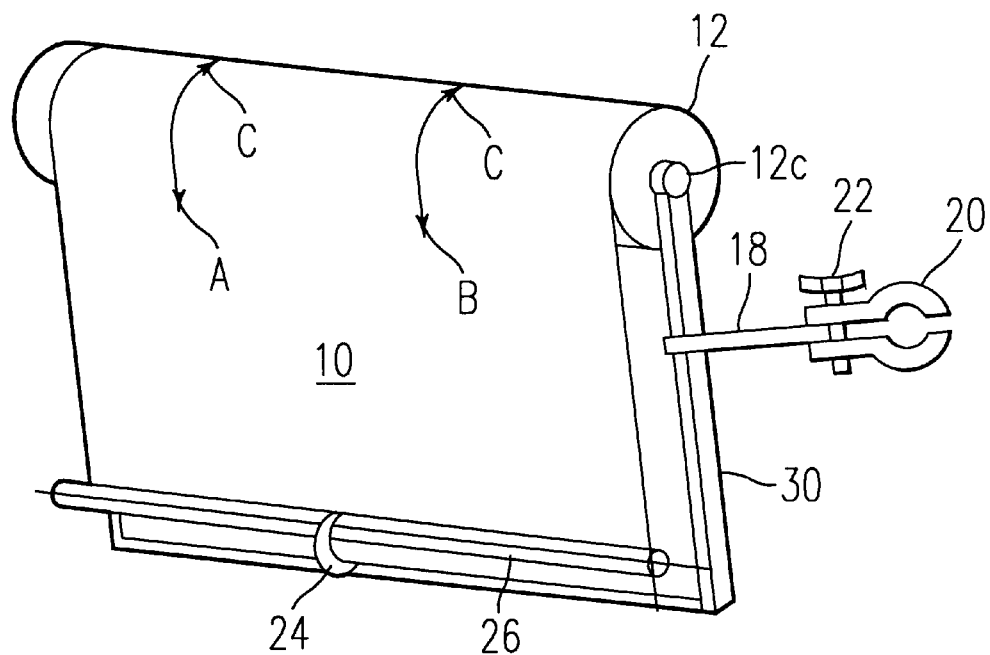
FIG. 4 shows a perspective view of a second embodiment.

FIG. 1 shows a roll of a filter 10 mounted on a spring-loaded roller 12. The filter 10 is a thin cellophane-type material which selectively blocks out a 350 to 550 nm wavelength of light while providing 88% transmission of the total amount of light. The filter 10 is sold in rolls by Rosco Laboratories, Inc., of Stamford, Conn. The preferred filter is identified as Roscolux #12 and has a straw color.

The filter 10 is pulled over a front roller 14 in a direction of a first arrowhead A and then down in a direction of a second arrow head B. The spring-loaded roller 12 is connected to the front roller 14 by a brace 16 which connects a center 12c of rotation for the roller 12 to a center 14c of rotation for the roller 14. A rod 18 descends downwardly from the brace 16 and carries at its lower end a C-clamp 20 which is adjustable by a wing nut 22 for attachment around an existing light handle (not shown).

When the filter 10 is either pulled down or rolled back up, a user grasps a disposable tab 24 and either pulls or pushes in a desired direction. For example, in the same manner as a window shade, the filter 10 is pulled down slightly and then outwardly before being released so that the roll of the filter 10 will be automatically rewound in a direction of arrow heads C onto the spring-loaded roller 12. A cross bar 26 is clipped along a bottom edge of the filter 10 and acts as a weight to keep the filter 10 straight, taut and unwrinkled. The disposable tab 24 is detachably fitted to the cross bar 26 at its center. Opposite ends of the cross bar 26 travel in a track guide 28 provided on opposite sides of a window-like frame 30 which is secured to and descends from the brace 16 at the center 14c of the front roller 14.

The window-like frame 30 is better seen in FIG. 2 where an arrow D indicates a downward direction of movement for the filter 10. The frame 30 has a lower sill 32 through which there is bored a hole 34 into which the tab 24 is hooked so that the filter 10 may be retained in the frame 30.

In FIG. 3, there is shown a side view of the invention. The tab 24 is seen at the bottom edge of the filter 10. For the sake of simplicity, the cross bar 26 and the frame 30 are not illustrated. The filter 10 extends from the spring-loaded roller 12 over the front roller 14. From the brace 16, the rod 18 extends downwardly so that the C-clamp 20 may be adjustably tightened around a handle H of a light L that is shined through the filter 10 onto the face of a patient P. As discussed previously, the filter 10 blocks out undesired light having a wavelength of 350 to 550 nm. When the dentist does not want the wavelength emitted by the light L to cure the composite being worked into a cavity, the filter 10 is pulled down to screen out the particularly unwanted wavelength of 400–500 nm. On the other hand, when the dentist wants to cure the composite in place, a special light gun is used to harden the composite. Also, the filter 10 may be retracted like a window shade up to the roller 14 so that the 400 to 500 nm wavelength emitted by the light L may shine onto a tooth of the patient P.

Figure 5:
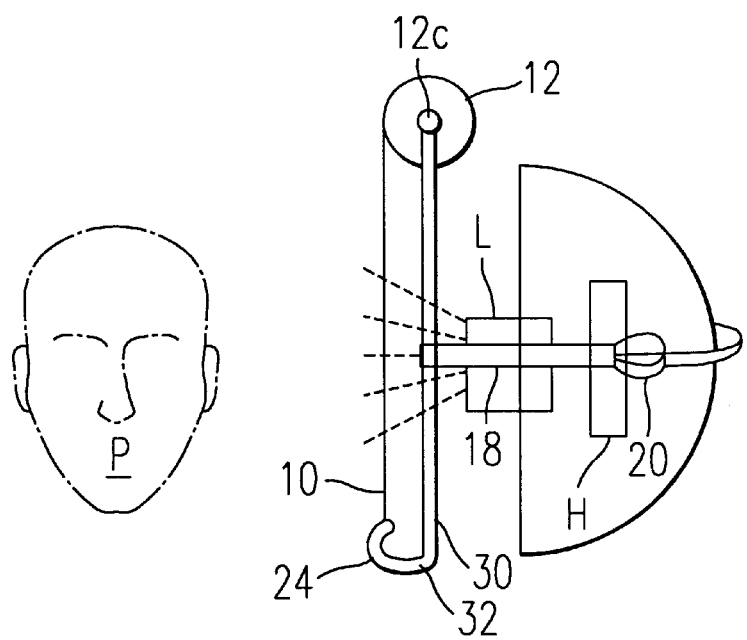
FIG. 5 shows a side elevational view of the second embodiment.

A simpler second embodiment is shown in FIGS. 4 and 5. In FIG. 4, the spring-loaded roller 12 is attached at its center 12c to the frame 30. The filter 10 moves either down in the direction of the arrow heads A and B or up in the direction of the arrow heads C. Unlike the first embodiment, the cross bar 26 in this second embodiment does not travel in any track guides in the frame 30. Along the bottom edge of the filter 10, the cross bar 26 has the disposable tab 24 attached at its center point. The rod 18 is secured directly to one side of the frame 30 and the C-clamp 20 is connect to one end of the rod 18. The wing nut 22 adjusts the tightness of the C-clamp 20. A second rod 18 and a second C-clamp 20 may be secured to another parallel side of the frame 30 hidden behind the filter 10 in FIG. 4.

In FIG. 5, the one rod 18 is seen to be secured to the near side of the frame 30 which descends from the center 12c of the roller 12. At the lower sill 32 of the frame 30, the tab 24 is hooked therein so that the filter 10 is held in place. The C-clamp 20 is tightened onto the handle H for the light L which emits the wavelength between 400 and 500 nm through the open frame 30 and also through the filter 10 so that the wavelength emitted by the light L may shine onto the tooth of the patient P. When the filter 10 is pulled down and hooked by the tab 24 onto the lower sill 32 of the frame 30, the 400 to 500 nm wavelength is selectively screened out and the composite being placed into the mouth of the patient P is not cured. In order to cure the composite, the dentist aims the light gun at the site. Thus, the dentist can work with both hands free while simultaneously preventing cross contamination between patients and staff members because the filter 10 itself is not handled by anyone.

Once the present invention is attached to the handle H of the light L, it is usually unnecessary to remove it again. Also, because the frame 30 is open, a dental assistant may easily change the light L when it burns out simply by reaching through the open window-like frame 30 which is about one foot wide.

Clearly, numerous modifications and variations of the present invention are possible in light of the above teachings. For example, the frame 30 may extend above the roller 12 so that it is necessary to pull the tab 24 upwardly to place the filter 10 in front of the light L of the dental lamp. In two more alternative embodiments, the frame 30 may extend along a side of the roller 12 so that it is necessary to pull the tab 24 either to one side or to an opposite side to place the filter 10 in front of the light L of the dental lamp. Thus, it is to be understood that the invention may be practiced otherwise than as specifically described herein.

What is claimed as new and desired to be secured by Letters Patent of the United States is:

1. A light-filtering apparatus for attachment to a dental lamp, said apparatus comprising:
   a. a filter that selectively blocks out an undesired effect of a wavelength of light for curing a dental material;
   b. a spring-loaded roller carrying the filter;
   c. a support structure attached to the roller; and
   d. means attached to the filter and configured to place the filter in front of the
   dental lamp when the means is operated by a user;
   whereby contamination which may occur from direct human contact is prevented.

2. A light-filtering apparatus according to claim 1, wherein the undesired effect comprises a premature hardening of the dental material.

3. A light-filtering apparatus according to claim 1, wherein the wavelength of light ranges from 350 to 550 nanometers.

4. A light-filtering apparatus according to claim 3, wherein the wavelength of light ranges from 400 to 500 nanometers.

5. A light-filtering apparatus according to claim 1, wherein the means comprises a tab pulled by the user.

6. A light-filtering apparatus according to claim 1, wherein the means comprises a disposable tab configured to be discarded after use.

7. A light-filtering apparatus for attachment to a dental lamp, said apparatus comprising:
   a. a filter that blocks out light having a 350 to 550 nanometer wavelength;
   b. a spring-loaded roller carrying the filter;
   c. a window-like frame attached to the roller; and
   d. a tab attached to the filter and configured to place the filter in front of the dental lamp when the tab is pulled by a user.

8. A light-filtering apparatus according to claim 7, wherein the filter is wound on a roll.

9. A light-filtering apparatus according to claim 7, wherein the frame descends downwardly from a center of rotation of the roller.

10. A light-filtering apparatus according to claim 7, further comprising a cross bar disposed at the base of said filter, wherein the tab is attached to the filter by said cross bar from which the tab is detachable.

11. A light-filtering apparatus according to claim 7, further comprising:
   e. a rod secured to a side of the frame and configured to carry a clamp that is adjustably attached to a handle for the dental lamp.

12. A light-filtering apparatus according to claim 7, wherein the tab comprises a disposable tab configured to be discarded after use.

13. A light-filtering apparatus for attachment to a dental lamp, said apparatus comprising:
   a. a filter that blocks out light having a 400 to 500 nanometer wavelength;
   b. a spring-loaded roller holding one end of the filter, said spring-loaded roller having a center of rotation;
   c. a second roller secured to the spring-loaded roller and configured so that another end of the filter passes thereover;
   d. a window-like frame attached to the second roller; and
   e. a tab attached to the other end of the filter and configured to place the filter in front of the dental lamp when the tab is pulled by a user.

14. A light-filtering apparatus according to claim 13, wherein the filter is wound on a roll.

15. A light-filtering apparatus according to claim 13, wherein the frame descends downwardly from a center of rotation of the second roller.

16. A light-filtering apparatus according to claim 13, further comprising a cross bar disposed at the other end of said filter, wherein the tab is attached to the filter by said cross bar which travels at opposite ends in a track guide provided on opposite sides of the frame, said tab being detachable from said cross bar.

17. A light-filtering apparatus according to claim 13, further comprising:
   f. a brace connected between the spring-loaded roller and the second roller;
   g. a rod secured to the brace; and
   h. a clamp carried by the rod and attached adjustably to a handle for the dental lamp.

18. A light-filtering apparatus according to claim 13, wherein the tab comprises a disposable tab configured to be discarded after use.

* * * * *